US005279593A

United States Patent [19]

Hiltebrandt

[11] Patent Number: 5,279,593

[45] Date of Patent: Jan. 18, 1994

[54] TROCAR SLEEVE

[75] Inventor: Siegfried Hiltebrandt, Knittlingen, Fed. Rep. of Germany

[73] Assignee: Richard Wolf GmbH, Knittlingen, Fed. Rep. of Germany

[21] Appl. No.: 806,965

[22] Filed: Dec. 12, 1991

[30] Foreign Application Priority Data

Feb. 12, 1991 [DE] Fed. Rep. of Germany ....... 4104193

[51] Int. Cl.[5] ........................................ A61M 5/00

[52] U.S. Cl. ........................................ 604/264; 128/3; 128/4; 604/33; 604/158; 604/164; 604/165; 604/166; 604/167; 604/169

[58] Field of Search .................. 251/116, 297; 604/33, 604/158, 164, 165, 166, 167, 169, 171, 249, 264, 272, 273, 275, 280; 128/3, 4

[56] References Cited

U.S. PATENT DOCUMENTS 1,213,001 1/1917 Philips ................................ 604/165
3,476,133 11/1969 Stedfeld ............................. 251/297
4,650,470 3/1987 Epstein ................................. 604/33
4,972,827 11/1990 Kishi et al. ............................ 128/3

FOREIGN PATENT DOCUMENTS 0323018 7/1989 European Pat. Off. .
1769525 7/1958 Fed. Rep. of Germany .
4002235 8/1990 Fed. Rep. of Germany .
3923243 1/1991 Fed. Rep. of Germany .
8909072 10/1989 PCT Int'l Appl. .

*Primary Examiner*—C. Fred Rosenbaum
*Assistant Examiner*—Noelle Kent Gring
*Attorney, Agent, or Firm*—Panitch Schwarze Jacobs & Nadel

[57] ABSTRACT

The invention relates to a trocar sleeve having a piston of a piston valve which can be brought into the open position against spring action by means of pressure on an actuation handle, which piston has a bore corresponding to the diameter of the access channel of the trocar sleeve. The valve piston can be fixed in its open position in the valve housing against its spring loading by a catch which can be released by hand.

5 Claims, 2 Drawing Sheets

TROCAR SLEEVE

BACKGROUND OF THE INVENTION (a) Field of the Invention

The invention relates to a trocar sleeve having a valve piston (trumpet valve) which can be brought into the open position against spring action by means of pressure on the actuation handle, which valve piston has a bore corresponding to the diameter of the access channel of the trocar sleeve.

(b) Description of the Prior Art

In such generally known trocar sleeves fitted with a trumpet valve (hand-actuated piston valve), the trumpet valve standing under permanent spring tension closes the channel of the trocar sleeve in a gas-tight manner when the trocar is removed and when instruments are exchanged.

However, known trocar sleeves of this type have the disadvantage that the trumpet valve standing under permanent spring tension in its channel presses on the instrument introduced, and hence inhibits its rotatability and its ability for longitudinal displacement. The sensitive handling of the instrument during endoscopy is thus impaired. In addition, damage to the instrument surface may thus occur, in particular for instruments with isolated surfaces.

The object of the invention is therefore to design a trocar sleeve with trumpet valve, so that the spring-loaded valve piston does not inhibit the mobility of an instrument when it is guided through the trocar sleeve and does not damage its surface, and in that the access channel of the trocar sleeve can be closed quickly in a gas-tight manner by means of simple operation when instruments are changed.

SUMMARY OF THE INVENTION

This object is achieved in accordance with the invention by a trocar sleeve having a piston of a piston valve which can be brought into the open position against spring action by means of pressure on an actuation handle, which piston has a bore corresponding to the diameter of the access channel of the trocar sleeve, wherein the valve piston can be fixed in its open position in the valve housing against its spring loading by a catch which can be released by hand.

In a specific solution, the cylindrical piston part accommodating the piston spring loading is provided with at least one recess near its free external end, into which one ball movably mounted to be radially spring-loaded in the valve housing wall engages in each case with a peripheral part, and the valve piston can be displaced by means of a driver which can be actuated by hand in the direction of the piston spring action to release the ball catch.

The recess near the external end of the cylindrical piston part suitably consists of a circular groove, into which at least one catch ball mounted to be radially spring-loaded in the valve housing wall can engage with a peripheral part.

The catch may consist of: a spring-pretensioned double-armed lever, which is pivoted at the valve housing on the side of the trocar sleeve facing the valve handle; and a catch pin, which is pivoted at the lever and in the open position of the valve cooperates with the piston thereof with a locking action. Advantageously, the catch pin and the piston are each provided with an abutting surface.

BRIEF DESCRIPTION OF THE DRAWINGS

Preferred embodiments of this invention will now be described, by way of example only, with reference to the drawings in which.

DESCRIPTION OF THE PREFERRED EMBODIMENT

Figure 1:
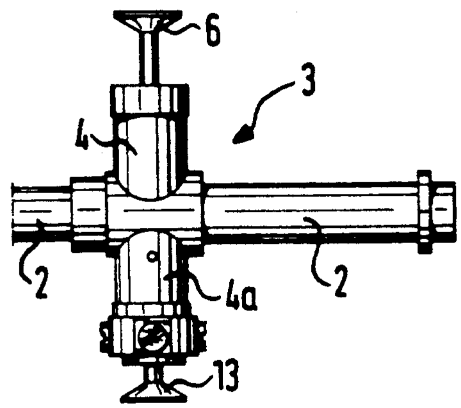
FIG. 1 shows a side view of a trocar sleeve with trumpet valve in the closed position.
Figure 2:
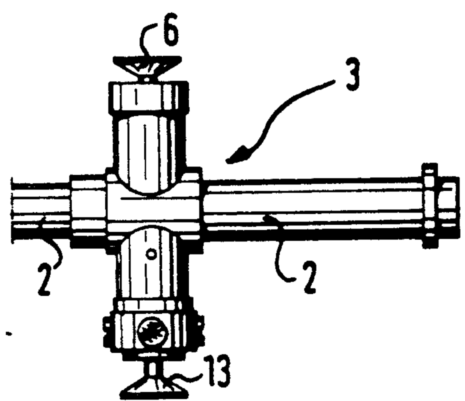
FIG. 2 shows the same view with trumpet valve in the open position.
Figure 3:
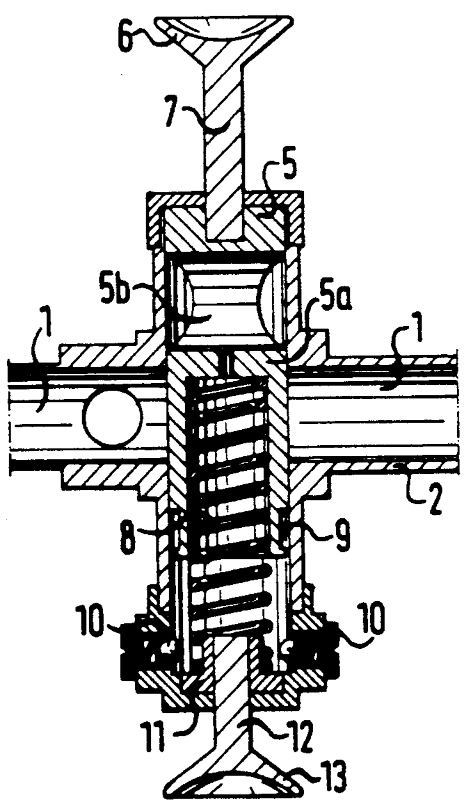
FIG. 3 shows an enlarged section through the trumpet valve according to FIG. 1.

Referring to FIGS. 1 to 4 of the drawings, a known trumpet valve 3, which consists of a housing 4, 4*a* with piston 5 which can be displaced in it, is arranged in the access channel 1 of a trocar sleeve 2. The piston 5 is pressed into the closed position by a rod 7 provided with handle 6 by means of a spring 8, so that the cylindrical part 5*a* of the piston accommodating the spring 8 closes the trocar sleeve channel in a sealing manner. The piston 5 is also provided with an access bore 5*b* corresponding to the diameter of the access channel 1 of the trocar sleeve 2.

Figure 4:
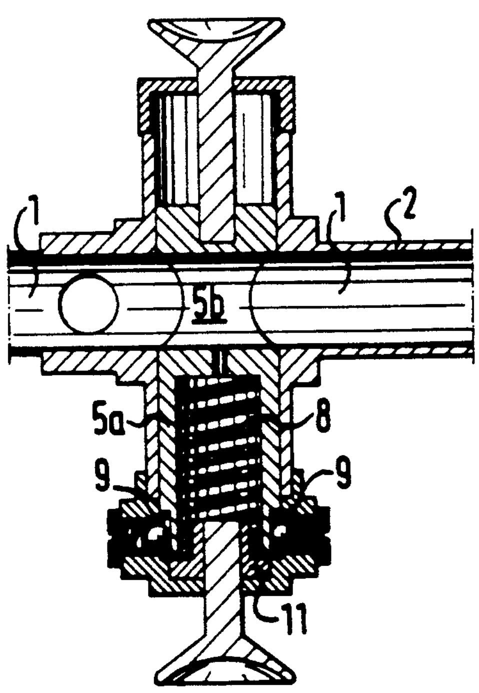
FIG. 4 shows an enlarged section through the trumpet valve according to FIG. 2.

According to the invention the cylindrical piston part 5*a* is provided with one or more peripheral recesses or with a peripheral groove 9 near a free external end, and the valve housing 4 is provided with radial bores at the lower end for receiving one or more catch balls 10 spring-loaded radially to the piston axis and which engage with a peripheral part in the peripheral groove of the piston 5, 5*a* to fix the position thereof, so that the piston is pressed by means of pressure on the handle 6 into the open position according to FIG. 4, in which the bore 5*b* of the piston 5 is aligned with the access channel 1 of the trocar sleeve 2. In this fixed open position, instruments may be introduced into the body cavity through the trocar sleeve without the mobility of the instruments being inhibited or damaged within the trocar sleeve.

In order to be able to close the channel 1 simply and quickly when changing the instruments, a disc 11 or a piston, which is connected to a rod 12 with handle 13 held by the closure of the housing part 4*a*, is mounted in the housing part 4*a*. Pressure on the handle 13 causes the disc 11 to displace the piston 5, 5*a* against the action of the catch balls 10 then pushed back from the groove 9, so that the piston becómes free and is pressed back into the closed position corresponding to FIG. 3 by means of its spring loading 8, whereupon the access channel 1 of the trocar sleeve 2 is sealed in a gas-tight manner from the body cavity.

Figure 6:
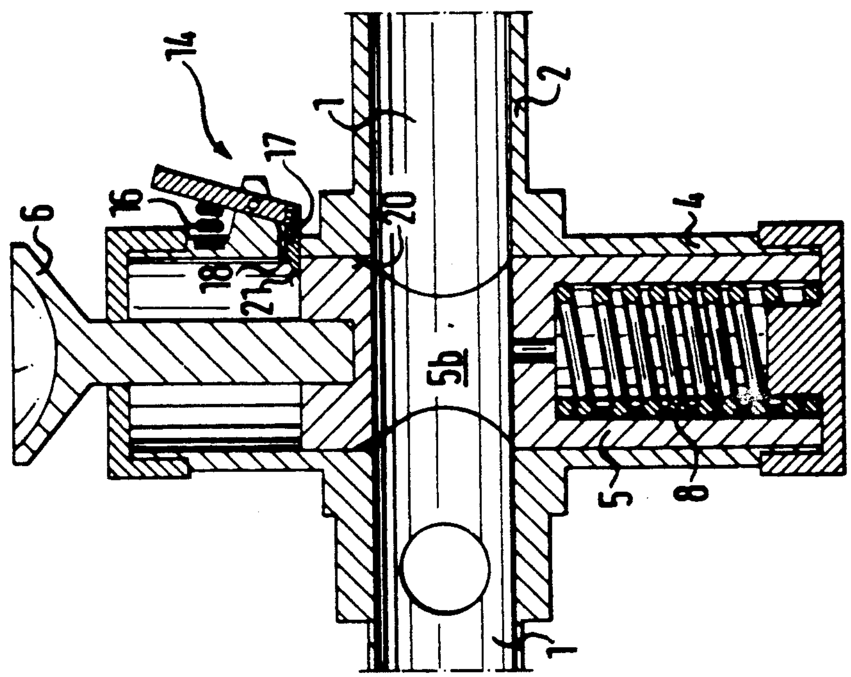
FIG. 6 shows a section through the trumpet valve according to FIG. 5 in open position.
Figure 5:
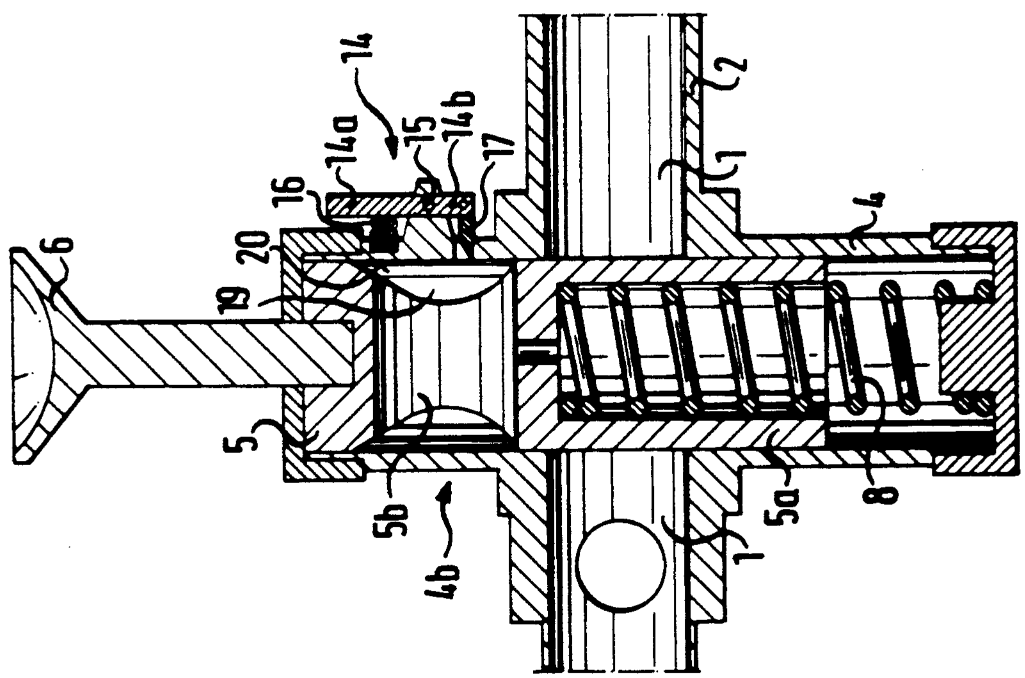
FIG. 5 shows a section through the trumpet valve in a further embodiment in closed position.

According to a further embodiment of the invention, the catch is provided in the upper valve housing part 4*b* to fix the valve piston 5, 5*a*. In accordance with the invention, as shown in FIGS. 5 and 6, a double-armed lever 14 is pivotably attached to the upper valve housing part 4*b* around a pin 15, wherein one lever arm 14*a* is supported against the valve housing by means of a spring 16 and the other lever arm 14b is connected to a pin 17 via a joint. The pin 17 projects through a bore 18 into the valve housing and thus forms the catch for the piston 5 pressed into the open position, as shown in FIG. 6. In this position the bore 5b of the piston 5 is again aligned with the access channel 1 of the trocar sleeve and the mobility of instruments introduced into the trocar sleeve remains uninhibited and there is no damage within the trocar sleeve.

For quick and simple closing of the access channel of the trocar sleeve, for example when changing instruments, the lever 14 is actuated against the pressure of the spring 16, whereupon the pin 17 is withdrawn from the interior of the valve housing 4 into the bore 18 so far that the valve piston 5 may slide into the closed position shown in FIG. 5 under the action the recovery force of the spring 8. The access channel 1 of the trocar sleeve is thus sealed again in a gas-tight manner. After releasing the lever 14, the pin 17 is moved forward through the bore 18 into the cavity 19 situated in the region of the piston bore 5b, between valve housing 4 and piston 5, under the recovery force of the spring 16.

For renewed change-over into the open position of the trocar sleeve of the invention, the pin 17 is withdrawn from the cavity 19 into the bore 18 by actuating the lever 14 and pressure on the handle 6 then moves the piston 5 into the open position and in this position, after releasing the lever 14 as described above, is fixed in the open position.

The open position may also only be attained by actuating the piston 5 by means of the handle 6, if, according to an advantageous design of this second embodiment, the piston 5 and the pin 17 are provided with corresponding abutting surfaces 20 and 21. When actuating the piston from the closed position, these corresponding abutting surfaces 20, 21 slide past one another and the pin 17 is pressed back into the bore 18 and springs into the position shown in FIG. 6 due to the recovery force of the spring 16 after the piston 5 has passed into the bore 18, whereupon the piston 5 is fixed again in the open position.

Whilst particular embodiments of the invention have been described, it should be appreciated that the invention is not limited thereto but includes all modifications and variations falling within its scope.

I claim:

1. A trocar sleeve having an access channel, said access channel having a predetermined diameter, said sleeve including a piston valve having a housing and a piston movably mounted within said housing, said piston including a bore extending therethrough, said bore having a diameter which corresponds to said predetermined diameter of said access channel, said piston being movable within said housing between an open position wherein said bore and access channel are aligned and a closed position wherein said bore and access channel are unaligned, said piston being biased towards said closed position by a spring disposed within said housing, said piston including a handle extending therefrom for moving said piston, and said valve including a hand releasable catch disposed within said housing for retaining said piston in said open position.

2. The trocar sleeve as recited in claim 1 wherein said piston included a recess proximate one end thereof, said catch including a spring loaded ball positioned within said recess when said piston is in said open position for retaining said piston in said open position, said valve further including a hand actuated driver for moving the piston from the open position to the closed position and for releasing the spring loaded ball from said recess.

3. The trocar sleeve as recited in claim 2 wherein said recess comprises a circular groove.

4. The trocar sleeve as recited in claim 1 wherein said catch comprises a lever pivotally mounted on said valve housing, said lever including a catch pin pivotably mounted to one end thereof, said lever being pivotable between a first position wherein said pin engages and retains said piston in the open position and a second position wherein said piston is free to move between said open and closed positions, said lever being spring biased to said first position.

5. The trocar sleeve as recited in claim 4 wherein when said lever is in said first position said piston abuts said pin at one end thereof.

* * * * *